US008709735B2

(12) United States Patent
Cooke et al.

(10) Patent No.: US 8,709,735 B2
(45) Date of Patent: Apr. 29, 2014

(54) β-2 MICROGLOBULIN AS A BIOMARKER FOR PERIPHERAL ARTERY DISEASE

(71) Applicants: Vermillion, Inc., Austin, TX (US); Board of Trustees of the Leland Stanford Junior University, Palo Alto, CA (US)

(72) Inventors: John P. Cooke, Palo Alto, CA (US); Eric T. Fung, Los Altos, CA (US); Elichiro Kimura, Nakano-ku (JP)

(73) Assignees: Vermillion, Inc., Austin, TX (US); Board of Trustees of of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/743,114

(22) Filed: Jan. 16, 2013

(65) Prior Publication Data
US 2013/0260389 A1 Oct. 3, 2013

Related U.S. Application Data

(62) Division of application No. 13/243,593, filed on Sep. 23, 2011, now Pat. No. 8,377,646, which is a division of application No. 12/972,867, filed on Dec. 20, 2010, now Pat. No. 8,053,204, which is a division of application No. 11/685,146, filed on Mar. 12, 2007, now Pat. No. 7,867,719.

(60) Provisional application No. 60/781,403, filed on Mar. 11, 2006, provisional application No. 60/863,951, filed on Nov. 1, 2006.

(51) Int. Cl.
*G01N 33/53* (2006.01)
*G01N 33/543* (2006.01)

(52) U.S. Cl.
USPC ........... 435/7.1; 435/7.21; 436/501; 436/506; 436/518; 422/430; 424/9.1; 530/300; 530/350

(58) Field of Classification Search
CPC .......... A61K 38/00; A61K 39/00; B01L 9/00; C07K 5/00; C07K 14/705; C07K 16/18; G01N 31/00; G01N 33/582; G01N 33/6893; G01N 33/54366
See application file for complete search history.

(56) References Cited

U.S. PATENT DOCUMENTS

| | | | |
|---|---|---|---|
| 7,867,719 B2 | 1/2011 | Cooke et al. | |
| 8,053,204 B2 * | 11/2011 | Cooke et al. | 435/7.21 |
| 8,377,646 B2 * | 2/2013 | Cooke et al. | 435/7.21 |
| 2003/0149997 A1 | 8/2003 | Hageman | |
| 2009/0042214 A1 | 2/2009 | Cooke et al. | |

FOREIGN PATENT DOCUMENTS

| | | |
|---|---|---|
| EP | 1 615 036 A1 | 1/2006 |
| WO | WO-01/06262 A1 | 1/2001 |
| WO | WO-2005047484 A2 | 5/2005 |
| WO | WO-2005121758 A1 | 12/2005 |
| WO | WO-2007106466 A2 | 9/2007 |
| WO | WO-2008057966 A2 | 5/2008 |

OTHER PUBLICATIONS

Schillinger, M., et al., "Joint Effects of C-Reactive Protein and Glycated Hemoglobin in Predicting Future Cardiovascular Events of Patients With Advanced Atherosclerosis," 2003 *Circulation AHA Journals*, pp. 2323-2328.
Standl, E., et al., "Predictors of 10-year macrovascular and overall mortality in patients with NDDM: the Munich General Practioner Project," 1996, *Diabetologia*, vol. 39, pp. 1540-1545.
Thongboonkerd, V., et al. "Protemoic analysis reveals alternations in the renal Kallikrein pathway during hypoxia-induced hypertension," 2002, *J. Biol. Chem.*, vol. 277, No. 33, pp. 34708-34716.
Zumrutdal, Al., et al. 2005, *Nephrology*, vol. 10, pp. 453-458.
Hampel, D., et al., 2001, *Journal of the American Society of Nephrology*, vol. 12, pp. 1026-1035.
Tatiana, G., et al., 1994, *Renal Failure*, vol. 16, No. 3, pp. 383-390 (Abstract Only).
Galina, J., et al., 2004, *Thrombosis and Vascular Biology*, 2004, vol. 24, pp. 1359-1366.
Karlsson, H., et al., 2005, *Proteomics*, vol. 5, pp. 551-565.
O'Hare, A.M., et al.; "Cystatin C and incident peripheal arterial disease events in the elderly," 2005, *Arch. Intern Med.*, vol. 165, pp. 2666-2670.
Nedelkov, D., et al.; "Design and use of multi-affinity surfaces in biomolecular interaction analysis-mass spectrometry (BIA/MS): a step toward the design of SPR/MS arrays," 2003, *Journal of Molecular Recognition*, vol. 16, pp. 15-19.
Saijo, Y., et al.; "Relationships of β2-microglobulin to arterial stiffness in Japanese subjects," 2005, *Hypertens. Res.*, vol. 28, No. 6, pp. 505-511.
Galina, J., et al., 2004, *Thrombobis and Vascular Biology*, 2004, vol. 24, pp. 1359-1366.
Criqui et al., "The generalized nature of atherosclerosis: how peripheral arterial disease may predict adverse events from coronary artery disease," Vascular Medicine, 1998, vol. 3, pp. 241-245.
Tzoulaki, et al., C-Reactive protein, interleukin-6, and soluble adhesion molecules as predictors of progressive peripheral atherosclerosis in the general population: Edinburgh artery study, Circulation, (2005), vol. 112, pp. 976-981.
Wilson, et al., "BETA2-Microglobulin as a Biomarker in Peripheral Arterial Disease: Protemoic Profiling and Clinical Studies," Circulation, Sep. 18, 2007, vol. 116, pp. 1396-1403.
An Office Action issued on Dec. 6, 2011, and mailed on Dec. 12, 2011, for corresponding Japanese Patent Application No. JP 2009-500423.

* cited by examiner

*Primary Examiner* — Lisa Cook
(74) *Attorney, Agent, or Firm* — Saul Ewing LLP; Melissa Hunter-Ensor; Elbert Chiang

(57) ABSTRACT

The present invention provides β2 microglobulin as a biomarker for qualifying or assessing peripheral artery disease in a subject.

11 Claims, 10 Drawing Sheets

Patient Demographics

| | Control (n=43) | PAD (n=45) | p |
|---|---|---|---|
| Age (years) | 66.0 | 72.3 | <0.01 |
| Women (%) | 37 | 22 | 0.16 |
| CAD (%) | 17 | 33 | 0.14 |
| HTN (%) | 59 | 80 | 0.04 |
| Hyperlipidemia (%) | 51 | 82 | <0.01 |
| Diabetes (%) | 17 | 24 | 0.44 |
| Smoking (%) | 62 | 81 | 0.14 |
| ABI | 1 | 1 | <0.01 |
| BMI | 28 | 28 | 0.51 |

FIG. 1

Statistical Analysis Results

| Peak ID | Chip | Fraction | Expected MW | Calculated MW | Putative protein |
|---|---|---|---|---|---|
| H11219 | CM10 | 2 | 11,732 | 11,729 | Beta-2-microglobulin |
| L11240 | CM10 | 2 | 11,731 | 11,729 | Beta-2-microglobulin |
| H11722 | IMAC30 | 2 | 11,722 | 11,729 | Beta-2-microglobulin, most likely |
| C011771 | IMAC30 | 3 | 11,731 | 11,729 | Beta-2-microglobulin |
| H11811 | IMAC30 | 1 | 11,811 | 11,729 | Beta-2-microglobulin, most likely |
| C011958 | IMAC30 | 3 | 11,941 | 11,936 | Beta-2-microglobulin, SPA adduct |
| L13392 | CM10 | 1 | 13,339 | 13,343 | Cystatin C |
| L14755 | CM10 | 1 | 14,690 | 14,692 | Lysozyme C |
| H22519 | CM10 | 2 | 22,519 | Not available | most likely IgG light chain |
| L22999 | CM10 | 6 | 22,999 | Not available | Not determined |
| H36067 | CM10 | 5 | 36,067 | Not available | Not determined |

FIG. 3

Patient Demographics

| | PAD (n=20) | Control (n=20) | p |
|---|---|---|---|
| Age (years) | 72.25 ± 7.9 | 70.1 ± 5.2 | 0.31 |
| Female (%) | 25 | 25 | 1.00 |
| HTN (%) | 90 | 65 | 0.13 |
| Hyperlipidemia (%) | 85 | 30 | <0.01 |
| Diabetes (%) | 25 | 5 | 0.18 |
| Smoking (%) | 85 | 45 | 0.02 |
| BMI | 1.53 ± 0.60 | 1.51 ± 0.61 | 0.90 |
| GFR | 66.5 ± 20.5 | 76.6 ± 12.2 | 0.07 |
| ABI | 0.55 ± 0.22 | 1.15 ± 0.14 | <0.01 |

FIG 5

Univariate Predictors of ABI
(Linear Regression)

| | B | SE | p |
|---|---|---|---|
| Age | -0.008 | 0.009 | 0.35 |
| Gender | 0.059 | 0.130 | 0.65 |
| Smoking | -0.372 | 0.102 | <0.01 |
| HTN | -0.035 | 0.135 | 0.80 |
| Hyperlipidemia | -0.308 | 0.103 | <0.01 |
| Diabetes | -0.312 | 0.150 | 0.05 |
| BMI | 0.055 | 0.095 | 0.57 |
| GFR | 0.005 | 0.003 | 0.13 |
| Log $\beta 2M$ | -1.443 | 0.411 | <0.01 |

FIG. 8

Multiple Linear Regression

Dependent variable: ABI

| | B | SE | p |
|---|---|---|---|
| Smoking | -0.194 | 0.402 | <0.001 |
| Hiperlipedimia | -0.149 | 0.098 | 0.137 |
| Diabetes | -0.228 | 0.121 | 0.068 |
| Log plasma $\beta$ 2M | -1.315 | 0.576 | 0.029 |
| GFR | -0.003 | 0.004 | 0.530 |

β-2 MICROGLOBULIN AS A BIOMARKER FOR PERIPHERAL ARTERY DISEASE

CROSS-REFERENCES TO RELATED APPLICATIONS

This application is a divisional of U.S. patent application Ser. No. 13/243,593, filed Sep. 23, 2011 now U.S. Pat. No. 8,377,646, which claims priority to U.S. patent application Ser. No. 12/972,867, filed Dec. 20, 2010, now issued as U.S. Pat. No. 8,053,204, which claims priority to U.S. patent application Ser. No. 11/685,146, filed Mar. 12, 2007, now issued as U.S. Pat. No. 7,867,719, which claims priority to U.S. Provisional Patent Application Ser. No. 60/781,403, filed Mar. 11, 2006, and U.S. Provisional Patent Application Ser. No. 60/863,951, filed Nov. 1, 2006, the disclosures of each of which are incorporated herein by reference in their entirety.

FIELD OF THE INVENTION

The invention relates generally to clinical diagnostics.

BACKGROUND OF THE INVENTION

Atherosclerosis is the accumulation of lipid-fibrin plaques on the luminal wall of vascular endothelial cells. The presence of atherosclerotic plaques can severely diminish vascular flow to target organs, leading to morbidity and mortality. Atherosclerotic plaques may occur in coronary arteries (coronary artery disease, "CAD", which can cause angina and heart attacks), in carotid arteries (carotid artery disease, which can cause stroke), and in arteries of the limb (usually affecting the leg arteries, also known as peripheral artery disease, "PAD"). Individuals may have narrowings in one or more of these regions. There are approximately 15 million individuals in the US with CAD; 8 million people with PAD; and about 5 million people with carotid artery disease. Whereas carotid and coronary artery disease are usually recognized by physicians, the diagnosis of PAD is usually missed.

The PARTNERS trial was a recent screening study which examined the prevalence of PAD in smokers or diabetics over the age of 55, or any individual over the age of 70, which were visiting their primary practitioner for a routine visit (Hirsch A T et al., "Peripheral arterial disease detection, awareness, and treatment in primary care," JAMA, 286: 1317-24 (2001)). In over 7000 patients that were screened, over 25% were found to have PAD, as detected by an ankle pressure measurements. Unfortunately, only ⅓ of these patients had previously been diagnosed. The majority had been unrecognized by their doctors as having PAD. PAD is commonly under-diagnosed and under-treated in part because many patients do not manifest the classic symptomatology. Exertional leg pain relieved by rest is only noted by 10-30% of patients (Hirsch et al., above). As a consequence, appropriate treatment for atherosclerosis is not initiated in many of these patients.

Because PAD patients are underdiagnosed and under-treated, they are at higher risk for cardiovascular death. Untreated PAD can lead to decreased mobility, ulcers, gangrene, and may ultimately require amputation of the affected extremity. Patients with PAD are at increased risk from myocardial infarction, cerebrovascular attack, aortic aneurysm rupture, and vascular death (Criqui M H et al, "The epidemiology of peripheral arterial disease: importance of identifying the population at risk," Vasc Med., 2:221-6 (1997); Meijer WT et al., "Peripheral arterial disease in the elderly: The Rotterdam Study," Arterioscler Thromb Vasc Biol., 18:185-92 (1998)).

A useful screening test for PAD is the ankle-brachial index ("ABI"). The ABI requires that the blood pressure be taken at the arm, and at the ankle. One calculates the ratio of the systolic pressure in the lower extremity to that in the upper extremity. In most healthy individuals, the ratio is close to 1 (i.e., 0.90 or greater) while in patients with a ratio less than 0.90, PAD is diagnosed. Generally, the lower the ratio, the more severe the disease. To assess the pressure at the ankle, one needs to use special equipment, i.e., a Doppler ultrasound probe. A simple stethoscope will not suffice because the leg vessels of adults tend to be stiffer than those in the arm, and do not generate Korotkoff sounds during deflation of the blood pressure cuff. Unfortunately, the Doppler ultrasound equipment requires special training, and is not used in the offices of primary practitioners. Accordingly, PAD is usually not diagnosed. Moreover, in patients with diabetes, who constitute over 30% of patients with PAD, poor vascular compressibility may cause the ABI test to yield false negatives.

PAD, when diagnosed early, is amenable to treatments which slow progression of the disease. Also, medications known to prevent heart attacks and strokes in patients with atherosclerosis (e.g., anti-platelet agents, statins, angiotensin converting enzyme inhibitors) are underutilized in PAD patients. Therefore, a need exists for screening tests which will alert the clinician to the possibility that their patient may have PAD. In particular, a blood test for PAD would be helpful since it could be performed in a routine clinical setting.

SUMMARY OF THE INVENTION

The present invention provides, in one embodiment, a method for qualifying or assessing the risk for peripheral artery disease in a subject comprising measuring β2-microglobulin in a biological sample from the subject. In a related embodiment, one (a) measures β2-microglobulin in a biological sample from the subject, and (b) correlates the measurement or measurements with peripheral artery disease versus non-peripheral artery disease. In another related embodiment, the sample is a blood or blood derivative sample. In yet another related embodiment, the levels in the sample of one or more biomarkers in addition to β2-microglobulin are measured. In another related embodiment, the additionally measured biomarkers are cystatin C or lysozyme or both. In another related embodiment, the beta 2-microglobulin, cystatin C or lysozyme measurements are obtained by an immunoassay.

In another embodiment of the method for qualifying peripheral artery disease in a subject, cystatin C or lysozyme or both are measured in a biological sample from the subject, and the measurement is correlated with peripheral artery disease status.

In another embodiment of the method for qualifying peripheral artery disease status in a subject, the β2-microglobulin in the sample is measured by mass spectrometry. In yet another related embodiment, the mass spectrometry method is SELDI-MS.

In another embodiment of the method for qualifying peripheral artery disease status in a subject, β2-microglobulin in a sample from the subject is measured by a method other than mass spectrometry, such as an immunoassay.

In another embodiment of the method for qualifying or assessing the risk of peripheral artery disease status in a subject, the method comprises correlating the measured levels of β2-microglobulin in the subject by executing a software classification algorithm. In another embodiment, the method for qualifying peripheral artery disease status further comprises the step of reporting the status to the subject. In another embodiment, the method further comprises recording the status on a tangible medium. In yet another embodiment, the method further comprises managing subject treatment based on the subject's peripheral artery disease status. In yet another embodiment, the method further comprises measuring at least one biomarker after subject management and correlating the measurement with disease progression.

In another embodiment, the invention provides a method for determining the course of peripheral artery disease comprising (a) measuring, at a first time, β2-microglobulin in a biological sample from the subject; (b) measuring, at a second time, β2-microglobulin in a biological sample from the subject; and (c) comparing the first measurement and the second measurement, wherein the comparative measurements determine the efficacy of treatment for peripheral artery disease.

In another embodiment, the invention provides a kit comprising (a) a solid support comprising at least one capture reagent attached thereto, wherein the capture reagent binds β2-microglobulin; and (b) instructions for using the solid support to detect β2-microglobulin. In a related embodiment, the solid support comprising a capture reagent is a SELDI probe. In another related embodiment, the kit further comprises a standard reference of β2-microglobulin.

In another embodiment, the invention provides a software product comprising (a) code that accesses data attributed to a sample, where the data comprises a measurement of at least one biomarker in the sample, wherein at least one biomarker is beta-2-microglobulin; and (b) code that executes a classification algorithm that classifies the peripheral artery disease status of the sample as a function of the measurement.

Another embodiment of the invention provides a method comprising communicating to a subject a diagnosis relating to peripheral artery disease status determined from the correlation of at least one biomarker in a sample from the subject, wherein at least one biomarker is beta-2-microglobulin. In a related embodiment, the beta 2-microglobulin measurements are obtained by an immunoassay. In another related embodiment, the method the diagnosis is communicated to the subject via a computer-generated medium.

In yet another embodiment, the invention provides a method for qualifying peripheral artery disease status in a subject comprising (a) measuring at least one biomarker in a biological sample from the subject, wherein said at least one biomarker is selected from the group consisting of β2-microglobulin, lysozyme and cystatin C; and (b) further measuring one or more of the following criteria of said subject: C-reactive protein levels, total cholesterol levels, triglyceride levels, low density lipoprotein levels, high density lipoprotein levels, blood sugar, blood pressure, homocysteine levels, the ankle brachial index, interleukin levels, fibrinogen levels, lipoprotein (a) levels, 8-iso-prostaglandin F 2alpha (8-iso-PGF 2alpha), and soluble Fas levels; and (c) correlating said measurements (a) and (b) with peripheral artery disease versus non-peripheral artery disease. In certain embodiments, the correlating step will include entering one or more of the above-mentioned values into an algorithm that can then predict the risk of the individual having peripheral arterial disease. In another related embodiment, the beta 2-microglobulin, cystatin C or lysozyme measurements are obtained by an immunoassay.

In another embodiment, the invention provides a method for predicting a subject's responsiveness to a therapeutic regimen for treating peripheral artery disease, comprising: (a) first measuring at least one biomarker in a biological sample from the subject, wherein said at least one biomarker is selected from the group consisting of β2-microglobulin, lysozyme and cystatin C; and (b) after said first measuring step, administering an initial treatment in a therapeutic regimen for treating peripheral artery disease; and (c) after said treatment, measuring said at least one biomarker a second time; and (d) comparing said first and second measurements, wherein decreasing levels of said at least one biomarker correlate with an increased likelihood of a subject's responsiveness to said therapeutic regimen. In a related embodiment, the beta 2-microglobulin, cystatin C or lysozyme measurements are obtained by an immunoassay.

The invention additionally provides a method for identifying a compound that interacts with beta-2-microglobulin, wherein said method comprises (a) contacting beta-2-microglobulin with a test compound; and (b) determining whether the test compound interacts with beta-2-microglobulin.

Other preferred embodiments are described elsewhere herein and in the Claims. Additional features, objects and advantages of the invention and its preferred embodiments will become apparent from the detailed description, examples and claims that follow.

BRIEF DESCRIPTION OF THE DRAWINGS

FIG. 1 shows a table summarizing patients used in a screening study for PAD biomarkers. CAD, coronary artery disease; HTN, hypertension; ABI, ankle-brachial index; BMI, body mass index. The average measured ABI for PAD patients in the discovery study was 0.60±0.18; the average measured ABI for control patients was 1.06±0.10.

FIG. 3 shows a table summarizing data relating to the 11 proteins identified as significant in FIG. 2, using the SAM analysis. This analysis was confirmed by a second bioinformatics approach (Prediction Analysis for Microarrays or "PAM" (Tibshurani et al., *Proc. Natl. Acad. Sci. USA* (2002) 99:6567-72)).

FIG. 5 shows a table summarizing the two groups of patients used in the validation study (see, Example 2, herein, for more detail). GFR, glomerular filtration rate.

FIG. 8 shows the results of a linear regression analyses of ELISA-measured levels of beta 2-microglobulin and other patient traits.

FIG. 9 shows the results of a multivariate model created to assess the independent relationship between log beta 2-microglobulin and ABI.

DETAILED DESCRIPTION OF THE INVENTION

1. Introduction

Figure 2:
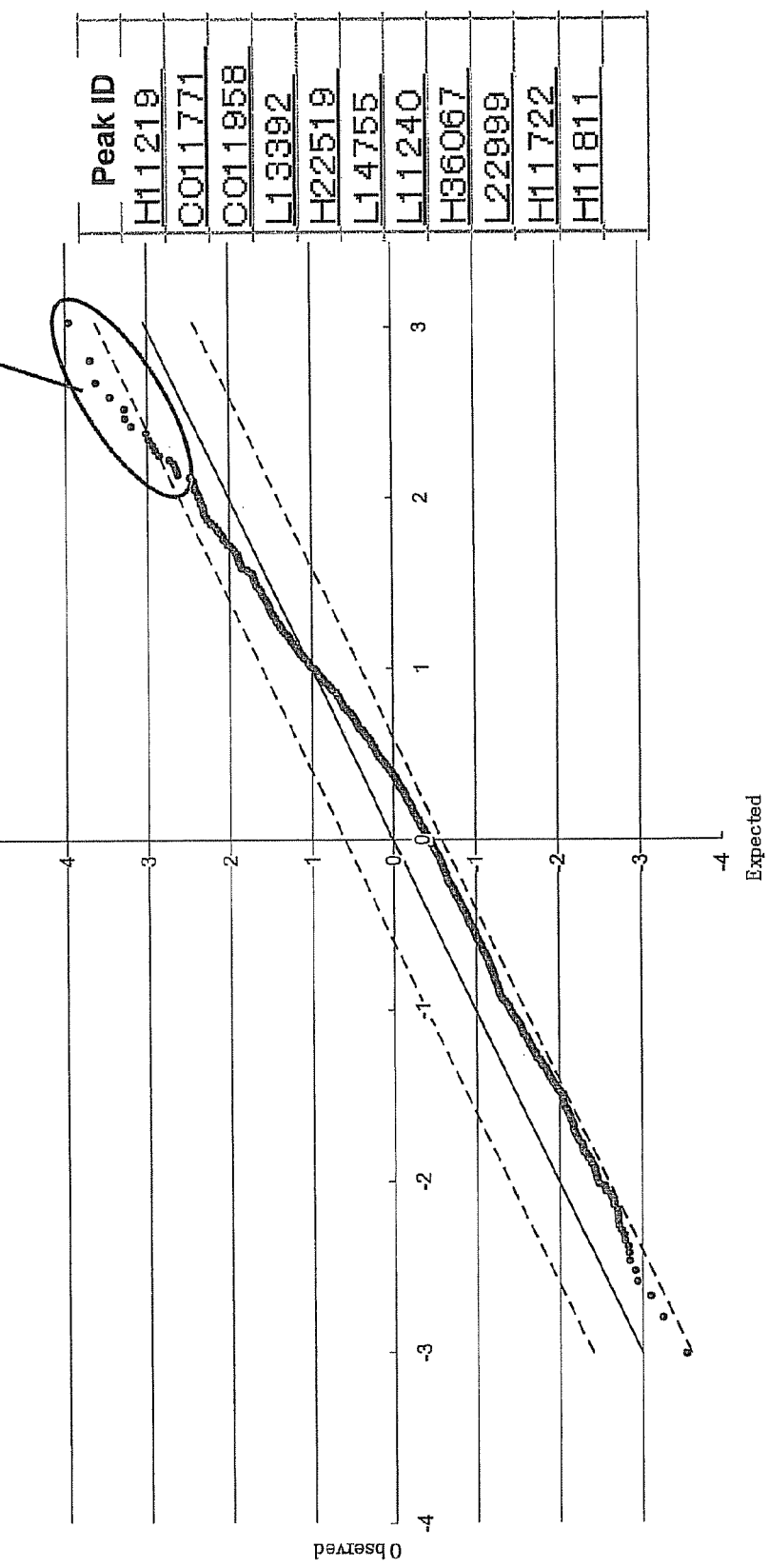
FIG. 2 shows results of an analysis of SELDI-TOF mass spectra using plasma samples obtained from patients described in FIG. 1. The data was analyzed with Statistical Analysis of Microarrays (SAM) software.

A biomarker is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. As such, they are useful as markers for disease (diagnostics), therapeutic effectiveness of a drug (theranostics) and of drug toxicity.

The biomarker of this invention were discovered, in part, using SELDI. Accordingly, they are characterized, in part, by their mass-to-charge ratio, the shape of the peak in a mass spectrum and their binding characteristics. These characteristics represent inherent characteristics of the biomolecule and not process limitations in the manner in which the biomolecule is discriminated.

The biomarker of this invention is characterized in part by their mass-to-charge ratio. The mass-to-charge ratio of each biomarker is provided herein. A particular molecular marker designated, for example, as "M11.7K" has a measured mass-to-charge ratio of 11.7K D. The mass-to-charge ratios were determined from mass spectra generated on a Ciphergen Biosystems, Inc. PBS II mass spectrometer or a Ciphergen PCS 4000 mass spectrometer. The PBS II is instrument has a mass accuracy of about +/−0.15 percent. Additionally, the instrument has a mass resolution of about 400 to 1000 m/dm, where m is mass and dm is the mass spectral peak width at 0.5 peak height. The PCS4000 instrument has a mass accuracy of about +/−0.12% raw data with an expected externally calibrated mass accuracy of 0.1% and internally calibrated mass accuracy of 0.01%. Additionally, the instrument has a mass resolution of about 1000 to 2000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII or PCS4000, taking the maximum and minimum mass-to-charge-ratio in the cluster, and dividing by two. Accordingly, the masses provided reflect these specifications.

The biomarker of this invention may be further characterized by the shape of its spectral peak in time-of-flight mass spectrometry.

The biomarker of this invention is also characterized by its binding characteristics to adsorbent surfaces. The binding characteristics of the biomarker are also described herein.

2. Biomarker for Peripheral Artery Disease

2.1. β-2 Microglobulin

We have discovered that β2-microglobulin is useful as a biomarker for peripheral artery disease. The mass of β2-microglobulin corresponds to a 11.7K Dalton biomarker for peripheral artery disease described in International Patent Publication WO 2005/121758 A1 (Fung et al.). β2-microglobulin is a 99 amino acid protein derived from a 119 amino acid precursor (GI:179318; SwissProt Accession No. P61769). β2-microglobulin is recognized by antibodies available from, e.g., Abcam (catalog AB759) (www.abcam.com, Cambridge, Mass.). Specifics of the β2-microglobulin biomarker are presented in Table 1, Table 2 and FIG. 3. The fractions referred to in Table 1 are the fractions in which the biomarker elutes from the QHyper DF column described in Example 1.

TABLE 1

| Marker | P-Value | Up or down regulated in peripheral artery disease | ProteinChip ® assay |
|---|---|---|---|
| β2-microglobulin (M11.7K) | <0.05 | Up | IMAC-Cu$^{++}$ (fractions 1-3) |
| (predicted mass: 11,729.17 D) | <0.05 | Up | CM10 (fraction 2) |
| Cystatin C (predicted mass: 13,343 D) | <0.05 | Up | CM10 (fraction 1) |
| Lysozyme (predicted mass: 14,692 D) | <0.05 | Up | CM10 (fraction 1) |

3. Biomarkers and Different Forms of a Protein

Proteins frequently exist in a sample in a plurality of different forms. These forms can result from either or both of pre- and post-translational modification. Pre-translational modified forms include allelic variants, splice variants and RNA editing forms. Post-translationally modified forms include forms resulting from proteolytic cleavage (e.g., fragments of a parent protein), glycosylation, phosphorylation, lipidation, oxidation, methylation, cysteinylation, sulphonation and acetylation. When detecting or measuring a protein in a sample, the ability to differentiate between different forms of a protein depends upon the nature of the difference and the method used to detect or measure. For example, an immunoassay using a monoclonal antibody (e.g., a monoclonal antibody which binds to an epitope of beta 2-microglobulin) will detect all forms of a protein containing the epitope and will not distinguish between them. However, a sandwich immunoassay that uses two antibodies directed against different epitopes on a protein will detect all forms of the protein that contain both epitopes and will not detect those forms that contain only one of the epitopes. In diagnostic assays, the inability to distinguish different forms of a protein has little impact when the forms detected by the particular method used are equally good biomarkers as any particular form. However, when a particular form (or a subset of particular forms) of a protein is a better biomarker than the collection of different forms detected together by a particular method, the power of the assay may suffer. In this case, it is useful to employ an assay method that distinguishes between forms of a protein and that specifically detects and measures a desired form or forms of the protein. Distinguishing different forms of an analyte or specifically detecting a particular form of an analyte is referred to as "resolving" the analyte.

Mass spectrometry is a particularly powerful methodology to resolve different forms of a protein because the different forms typically have different masses that can be resolved by mass spectrometry. Accordingly, if one form of a protein is a superior biomarker for a disease than another form of the biomarker, mass spectrometry may be able to specifically detect and measure the useful form where traditional immunoassay fails to distinguish the forms and fails to specifically detect to useful biomarker.

One useful methodology combines mass spectrometry with immunoassay. First, a biosepcific capture reagent (e.g., an antibody, aptamer or Affibody that recognizes the biomarker and other forms of it) is used to capture the biomarker of interest. Preferably, the biospecific capture reagent is bound to a solid phase, such as a bead, a plate, a membrane or a chip. After unbound materials are washed away, the captured analytes are detected and/or measured by mass spectrometry. (This method also will also result in the capture of protein interactors that are bound to the proteins or that are otherwise recognized by antibodies and that, themselves, can be biomarkers.) Various forms of mass spectrometry are useful for detecting the protein forms, including laser desorption approaches, such as traditional MALDI or SELDI, and electrospray ionization.

Thus, when reference is made herein to detecting a particular protein or to measuring the amount of a particular protein, it means detecting and measuring the protein with or without resolving various forms of protein. For example, the step of "measuring beta-2-microglobulin" includes measuring beta-2-microglobulin by means that do not differentiate between various forms of the protein (e.g., certain immunoassays) as well as by means that differentiate some forms from other forms or that measure a specific form of the protein. In contrast, when it is desired to measure a particular form or forms of a protein, e.g., a particular form of beta-2-microglobulin, the particular form (or forms) is specified. For example, "measuring beta-2-microglobulin (M11.7K)" means measuring beta-2-microglobulin M11.7K in a way that distinguishes it from other forms of beta-2-microglobulin.

4. Detection of Beta 2-Microglobulin

The β2-microglobulin, cystatin C and lysozyme biomarkers of the present invention can be detected by any suitable method. Detection paradigms include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In one embodiment, a sample is analyzed by means of a biochip. A biochip generally comprises a solid substrate having a substantially planar surface, to which a capture reagent (also called an adsorbent or affinity reagent) is attached. Frequently, the surface of a biochip comprises a plurality of addressable locations, each of which has the capture reagent bound there.

Protein biochips are biochips adapted for the capture of polypeptides. Many protein biochips are described in the art. These include, for example, protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK). Examples of such protein biochips are described in the following patents or published patent applications: U.S. Pat. No. 6,225,047 (Hutchens & Yip); U.S. Pat. No. 6,537,749 (Kuimelis and Wagner); U.S. Pat. No. 6,329,209 (Wagner et al.); PCT International Publication No. WO 00/56934 (Englert et al.); PCT International Publication No. WO 03/048768 (Boutell et al.) and U.S. Pat. No. 5,242,828 (Bergstrom et al.).

4.1. Detection by Mass Spectrometry

In a preferred embodiment, the biomarker of this invention is detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these.

In a further preferred method, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer. The analysis of proteins by LDI can take the form of MALDI or of SELDI 4.1.1. SELDI A preferred mass spectrometric technique for use in the invention is "Surface Enhanced Laser Desorption and Ionization" or "SELDI," as described, for example, in U.S. Pat. No. 5,719,060 and No. 6,225,047, both to Hutchens and Yip. This refers to a method of desorption/ionization gas phase ion spectrometry (e.g., mass spectrometry) in which an analyte (here, one or more of the biomarkers) is captured on the surface of a SELDI mass spectrometry probe.

SELDI also has been called is called "affinity capture mass spectrometry" or "Surface-Enhanced Affinity Capture" ("SEAC"). This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent is attached to the probe surface by physisorption or chemisorption. In certain embodiments the probes have the capture reagent already attached to the surface. In other embodiments, the probes are pre-activated and include a reactive moiety that is capable of binding the capture reagent, e.g., through a reaction forming a covalent or coordinate covalent bond. Epoxide and acyl-imidizole are useful reactive moieties to covalently bind polypeptide capture reagents such as antibodies or cellular receptors. Nitrilotriacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitrilotriacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen Biosystems, Inc. comprise surfaces having chromatographic or biospecific adsorbents attached thereto at addressable locations. Ciphergen ProteinChip® arrays include NP20 (hydrophilic); H4 and H50 (hydrophobic); SAX-2, Q-10 and (anion exchange); WCX-2 and CM-10 (cation exchange); IMAC-3, IMAC-30 and IMAC-50 (metal chelate); and PS-10, PS-20 (reactive surface with acyl-imidizole, epoxide) and PG-20 (protein G coupled through acyl-imidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitrilotriacetic acid functionalities (MAC 3 and IMAC 30) or O-methacryloyl-N,N-bis-carboxymethyl tyrosine functionalities (IMAC 50) that adsorb transition metal ions, such as copper, nickel, zinc, and gallium, by chelation. Preactivated ProteinChip arrays have acyl-imidizole or epoxide functional groups that can react with groups on proteins for covalent binding.

Such biochips are further described in: U.S. Pat. No. 6,579,719 (Hutchens and Yip, "Retentate Chromatography," Jun. 17, 2003); U.S. Pat. No. 6,897,072 (Rich et al., "Probes for a Gas Phase Ion Spectrometer," May 24, 2005); U.S. Pat. No. 6,555,813 (Beecher et al., "Sample Holder with Hydrophobic Coating for Gas Phase Mass Spectrometer," Apr. 29, 2003); U.S. Patent Publication No. U.S. 2003-0032043 A1 (Pohl and Papanu, "Latex Based Adsorbent Chip," Jul. 16, 2002); and PCT International Publication No. WO 03/040700 (Urn et al., "Hydrophobic Surface Chip," May 15, 2003); U.S. Patent Publication No. US 2003-0218130 A1 (Boschetti et al., "Biochips With Surfaces Coated With Polysaccharide-Based Hydrogels," Apr. 14, 2003) and U.S. Patent Publication No. U.S. 2005-059086 A1 (Huang et al., "Photocrosslinked Hydrogel Blend Surface Coatings," Mar. 17, 2005).

In general, a probe with an adsorbent surface is contacted with the sample for a period of time sufficient to allow the biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

In yet another method, one can capture the biomarkers with a solid-phase bound immuno-adsorbent that has antibodies that bind the biomarkers. After washing the adsorbent to remove unbound material, the biomarkers are eluted from the solid phase and detected by applying to a SELDI chip that binds the biomarkers and analyzing by SELDI.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

4.1.2. SEND

Another method of laser desorption mass spectrometry is called Surface-Enhanced Neat Desorption ("SEND"). SEND involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-ethoxy)silyl propyl methacrylate. In another embodiment, the composition is a co-polymer of α-cyano-4-methacryloyloxycinnamic acid and octadecylmethacrylate ("C 18 SEND"). SEND is further described in U.S. Pat. No. 6,124,137 and PCT International Publication No. WO 03/64594 (Kitagawa, "Monomers And Polymers Having Energy Absorbing Moieties Of Use In Desorption/Ionization Of Analytes," Aug. 7, 2003).

SEAC/SEND is a version of laser desorption mass spectrometry in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

4.1.3. SEPAR

Another version of LDI is called Surface-Enhanced Photolabile Attachment and Release ("SEPAR"). SEPAR involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker profile, pursuant to the present invention.

4.1.4. MALDI

MALDI is a traditional method of laser desorption/ionization used to analyze biomolecules such as proteins and nucleic acids. In one MALDI method, the sample is mixed with matrix and deposited directly on a MALDI chip. However, the complexity of biological samples such as serum or urine make this method less than optimal without prior fractionation of the sample. Accordingly, in certain embodiments with biomarkers are preferably first captured with biospecific (e.g., an antibody) or chromatographic materials coupled to a solid support such as a resin (e.g., in a spin column). Specific affinity materials that bind beta2-microglobulin is described above. After purification on the affinity material, the biomarkers are eluted and then detected by MALDI.

4.1.5. Other Forms of Ionization in Mass Spectrometry

In another method, the biomarkers are detected by LC-MS or LC-LC-MS. This involves resolving the proteins in a sample by one or two passes through liquid chromatography, followed by mass spectrometry analysis, typically electrospray ionization.

4.1.6. Data Analysis

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's ProteinChip® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

4.1.7. General Protocol for SELDI Detection of Biomarkers for Peripheral Artery Disease A preferred protocol for the detection of the biomarkers of the invention is as follows. The biological sample to be tested, e.g., serum, preferably is subject to pre-fractionation before SELDI analysis. This simplifies the sample and improves sensitivity. A preferred method of pre-fractionation involves contacting the sample with an anion exchange chromatographic material, such as Q HyperD (BioSepra, SA). The bound materials are then subject to stepwise pH elution using buffers at pH 9, pH 7, pH 5 and pH 4. The fractions in which the biomarkers are eluted are also indicated in Table 1, Table 2 (by pH) and FIG. 3. Various fractions containing the biomarker are collected.

The sample to be tested (preferably pre-fractionated) is then contacted with an affinity capture probe comprising an cation exchange adsorbent (preferably a CM10 ProteinChip array (Ciphergen Biosystems, Inc.)) or an IMAC adsorbent (preferably an IMAC30 ProteinChip array (Ciphergen Biosystems, Inc.)), again as indicated in Table 1, Table 2 and/or FIG. 3. The probe is washed with a buffer that will retain the biomarker while washing away unbound molecules (see Example 1, below). The biomarkers are detected by laser desorption/ionization mass spectrometry.

Alternatively, samples may be diluted, with or without denaturing, in the appropriate array binding buffer and bound and washed under conditions optimized for detecting each analyte.

Alternatively, if antibodies that recognize the biomarker are available, for example from Dako, U.S. Biological, Chemicon, Abcam and Genway. These can be attached to the surface of a probe, such as a pre-activated PS 10 or PS20 ProteinChip array (Ciphergen Biosystems, Inc.). These antibodies can capture the biomarkers from a sample onto the probe surface. Then the biomarkers can be detected by, e.g., laser desorption/ionization mass spectrometry.

Any robot that performs fluidics operations can be used in these assays, for example, those available from Tecan or Hamilton.

4.2. Detection by Immunoassay

In another embodiment of the invention, the biomarkers of the invention are measured by a method other than mass spectrometry or other than methods that rely on a measurement of the mass of the biomarker. In one such embodiment that does not rely on mass, beta 2-microglobulin is measured by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art. Beta 2-microglobulin antibodies and methods for detecting beta 2-microglobulin using standard assays are described in the art, e.g., Hilgert et al. (*Folia Biol (Praha)* (1984) 30:369-76). Examples of the use of these antibodies to detect increased levels of beta 2-microglobulin in PAD patients relative to normal patients are provided herein. Similar methods for the immunoassay detection of lysozyme and cystatin C are also known in the art.

This invention contemplates traditional immunoassays including, for example, sandwich immunoassays including ELISA or fluorescence-based immunoassays, other enzyme immunoassays and western blot. Nephelometry is an assay done in liquid phase, in which antibodies are in solution. Binding of the antigen to the antibody results in changes in absorbance, which is measured. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

5. Determination of Subject Peripheral Artery Disease Status

The biomarkers of the invention can be used in diagnostic tests to assess peripheral artery disease status in a subject, e.g., to assess the risk of a patient having peripheral artery disease. The phrase "peripheral artery disease status" includes any distinguishable manifestation of the disease, including non-disease. For example, peripheral artery disease status includes, without limitation, the presence or absence of disease (e.g., peripheral artery disease v. non-peripheral artery disease), the risk of developing disease, the stage of the disease, the progression of disease (e.g., progress of disease or remission of disease over time) and the effectiveness or response to treatment of disease.

The correlation of test results with peripheral artery disease status involves applying a classification algorithm of some kind to the results to generate the status. The classification algorithm may be as simple as determining whether or not the amount of beta-2-microglobulin measured is above or below a particular cut-off number. When multiple biomarkers or cardiovascular risk factors (e.g., the age, gender, blood pressure, blood sugar, and blood cholesterol) are used, the classification algorithm may be a linear regression formula. Alternatively, the classification algorithm may be the product of any of a number of learning algorithms described herein.

In the case of complex classification algorithms, it may be necessary to perform the algorithm on the data, thereby determining the classification, using a computer, e.g., a programmable digital computer. In either case, one can then record the status on tangible medium, for example, in computer-readable format such as a memory drive or disk or simply printed on paper. The result also could be reported on a computer screen.

5.1. Single Markers

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

β2-microglobulin shows a statistical difference in different peripheral artery disease statuses. Diagnostic tests that use these biomarkers alone or in combination show a sensitivity and specificity of at least 75%, at least 80%, at least 85%, at least 90%, at least 95%, at least 98% and about 100%. A test that has a high sensitivity but a low specificity may still be useful if its negative predictive value is high enough to exclude a diagnosis of PAD. An example of a clinically very useful test that has high sensitivity but low specificity is the ventilation-perfusion scan. A negative test virtually excludes pulmonary embolism since the negative predictive value is over 95%. Such a test result can reduce the need for further and more expensive testing.

β2-microglobulin, lysozyme and cystatin C are differentially present in peripheral artery disease, and, therefore, are each useful by themselves in methods of determining peripheral artery disease status. The method involves, first, measuring β2-microglobulin in a subject sample using the methods described herein, e.g., measurement by an immunoassay or capture on a SELDI biochip followed by detection by mass spectrometry and, second, comparing the measurement with a diagnostic amount or cut-off that distinguishes a positive peripheral artery disease status from a negative peripheral artery disease status. The diagnostic amount represents a measured amount of a biomarker above which or below which a subject is classified as having a particular peripheral artery disease status. For example, because beta-2-microglobulin is up-regulated in peripheral artery disease compared to normal, then a measured amount of beta-2-microglobulin above the diagnostic cutoff indicates an increased risk of peripheral artery disease. By contrast, a level may be low enough to virtually exclude PAD as a diagnosis. As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the biomarker in a statistically significant number of samples from subjects with the different peripheral artery disease statuses, as was done here, and drawing the cut-off to suit the diagnostician's desired levels of specificity and sensitivity.

5.2. Combinations of Markers

While individual biomarkers are useful diagnostic biomarkers, it has been found that a combination of biomarkers can provide greater predictive value of a particular status than single biomarkers alone. Specifically, the detection of a plurality of biomarkers in a sample can increase the sensitivity and/or specificity of the test. A combination of at least two biomarkers is sometimes referred to as a "biomarker profile" or "biomarker fingerprint." Accordingly, beta-2-microglobulin can be combined with other biomarkers for peripheral artery disease to improve the sensitivity and/or specificity of the diagnostic test. Examples of other biomarkers useful for screening for PAD are found in the PCT Application US2005/018728 (Inter. Pub. No. WO2005/121758), filed May 26, 2005.

5.3. Peripheral Artery Disease Status

Determining peripheral artery disease status typically involves classifying an individual into one of two or more groups (statuses) based on the results of the diagnostic test. The diagnostic tests described herein can be used to classify between a number of different states. The phrase "PAD status" includes distinguishing, inter alia, PAD v. non-PAD (e.g., normal) and/or PAD v. "long claudicator" PAD (LC PAD). A long claudicator is an individual with PAD that is less limited than other patients (i.e., the long claudicator can walk for more than 12 minutes on a treadmill using the Skinner-Gardner protocol). Based on this status, further procedures may be indicated, including additional diagnostic tests or therapeutic procedures or regimens.

5.3.1. Presence of Disease

In one embodiment, this invention provides methods for assessing the risk of peripheral artery disease in a subject (status: peripheral artery disease v. non-peripheral artery disease). The risk of peripheral artery disease is determined by measuring the relevant biomarker or biomarkers and then either submitting them to a classification algorithm or comparing them with a reference amount and/or pattern of biomarkers that is associated with the particular risk level.

5.3.2. Determining Risk of Developing Disease

In one embodiment, this invention provides methods for determining the risk of developing peripheral artery disease in a subject (status: low-risk v. high risk). Biomarker amounts or patterns are characteristic of various risk states, e.g., high, medium or low. The risk of developing a disease is determined by measuring the relevant biomarker or biomarkers and then either submitting them to a classification algorithm or comparing them with a reference amount and/or pattern of biomarkers that is associated with the particular risk level

5.3.3. Determining Stage of Disease

In one embodiment, this invention provides methods for determining the stage of disease in a subject. Each stage of a disease will have a characteristic amount of a biomarker or relative amounts of a set of biomarkers (a pattern). The stage of a disease is determined by measuring the relevant biomarker (e.g., beta 2-microglobulin) or biomarkers and then either submitting them to a classification algorithm or comparing them with a reference amount and/or pattern of biomarkers that is associated with the particular stage. For example, one can classify between early stage peripheral artery disease and non-peripheral artery disease.

5.3.4. Determining Course (Progression/Remission) of Disease

In one embodiment, this invention provides methods for determining the course of disease in a subject. Disease course refers to changes in disease status over time, including disease progression (worsening) and disease regression (improvement). Over time, the amounts or relative amounts (e.g., the pattern) of the biomarkers changes. For example, high beta-2-microglobulin levels, and/or high lysozyme levels and/or high cystatin C levels are correlated with PAD. Therefore, the trend of these markers, either increased or decreased over time toward diseased or non-diseased, can be used to monitor the course of the disease. Accordingly, this method involves measuring one or more biomarkers in a subject for at least two different time points, e.g., a first time and a second time, and comparing the change in amounts, if any. The course of disease is determined based on these comparisons.

5.4. Reporting the Status

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on β2-microglobulin and/or lysozyme and/or cystatin C in a test subject is communicated to the subject after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

5.5. Subject Management

In certain embodiments of the methods of qualifying or assessing peripheral artery disease status, the methods further comprise managing subject treatment based on the status. Such management includes the actions of the physician or clinician subsequent to determining peripheral artery disease status. For example, if a physician makes a diagnosis of peripheral artery disease, then a certain regimen of treatment may follow. A suitable regimen of treatment may include, without limitation, a supervised exercise program; control of blood pressure, sugar intake, and/or lipid levels; cessation of smoking, including any necessary counseling and nicotine replacement; and drug therapies including the administration of aspirin (with or without dipyridamole), clopidogrel, cilostazol, and/or pentoxifylline. Alternatively, a diagnosis of PAD might be followed by further testing to determine whether a patient is suffering from a specific form of PAD, or whether the patient is suffering from related diseases such as coronary artery disease. Also, if the diagnostic test gives an inconclusive result on PAD status, further tests may be called for.

6. Generation of Classification Algorithms for Qualifying Peripheral Artery Disease Status In some embodiments, data derived from the spectra (e.g., mass spectra or time-of-flight spectra) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", *IEEE*

*Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. Pat. No. 6,675,104 (Paulse et al., "Method for analyzing mass spectra").

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application No. 2002 0193950 A1 (Gavin et al., "Method for analyzing mass spectra"), U.S. Patent Application No. 2003 0004402 A1 (Hitt et al., "Process for discriminating between biological states based on hidden patterns from biological data"), and U.S. Patent Application No. 2003 0055615 A1 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, or for finding new biomarkers for peripheral artery disease. The classification algorithms, in turn, form the base for diagnostic tests by providing diagnostic values (e.g., cut-off points) for biomarkers used singly or in combination.

7. Compositions of Matter

In another aspect, this invention provides compositions of matter based on the biomarkers of this invention, e.g., the β2-microglobulin, lysozyme, cystatin C and other biomarkers listed in Table 1, Table 2 and FIG. 3.

In one embodiment, this invention provides the biomarker of this invention in purified form. Purified biomarkers have utility as antigens to raise antibodies. Purified biomarkers also have utility as standards in assay procedures. As used herein, a "purified biomarker" is a biomarker that has been isolated from other proteins and peptides, and/or other material from the biological sample in which the biomarker is found. The biomarkers can be isolated from biological fluids, such as urine or serum. Biomarkers may be purified using any method known in the art, including, but not limited to, mechanical separation (e.g., centrifugation), ammonium sulphate precipitation, dialysis (including size-exclusion dialysis), electrophoresis (e.g. acrylamide gel electrophoresis) size-exclusion chromatography, affinity chromatography, anion-exchange chromatography, cation-exchange chromatography, and methal-chelate chromatography. Such methods may be performed at any appropriate scale, for example, in a chromatography column, or on a biochip.

In another embodiment, this invention provides a biospecific capture reagent, optionally in purified form, that specifically binds a biomarker of this invention. In one embodiment, the biospecific capture reagent is an antibody. Such compositions are useful for detecting the biomarker in a detection assay, e.g., for diagnostics.

In another embodiment, this invention provides an article comprising a biospecific capture reagent that binds a biomarker of this invention, wherein the reagent is bound to a solid phase. For example, this invention contemplates a device comprising bead, chip, membrane, monolith or microtiter plate derivatized with the biospecific capture reagent. Such articles are useful in biomarker detection assays.

In another aspect this invention provides a composition comprising a biospecific capture reagent, such as an antibody, bound to a biomarker of this invention, the composition optionally being in purified form. Such compositions are useful for purifying the biomarker or in assays for detecting the biomarker.

In another embodiment, this invention provides an article comprising a solid substrate to which is attached an adsorbent, e.g., a chromatographic adsorbent or a biospecific capture reagent, to which is further bound a biomarker of this invention. In one embodiment, the article is a biochip or a probe for mass spectrometry, e.g., a SELDI probe. Such articles are useful for purifying the biomarker or detecting the biomarker.

8. Kits for Detection of Biomarkers for Peripheral Artery Disease

In another aspect, the present invention provides kits for qualifying peripheral artery disease status, which kits are used to detect biomarkers according to the invention. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of biospecfic capture reagents, the kit can comprise a solid support with a reactive surface, and a container comprising the biospecific capture reagent (e.g., an antibody for beta2-microglobulin).

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

9. Determining Therapeutic Efficacy of Pharmaceutical Drug

In another embodiment, this invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of β2-microglobulin (or lysozyme and/or cystatin C) changes toward a non-disease profile. For example, beta-2-microglobulin is increased in patients with PAD. Therefore, one can follow the effect of treatment (and other biomarkers) in the subject with PAD during the course of treatment. Accordingly, this method involves measuring one or more biomarkers in a subject receiving drug therapy, and correlating the amounts of the biomarkers with the disease status of the subject. One embodiment of this method involves determining the levels of the biomarkers for at least two different time points during a course of drug therapy, e.g., a first time and a second time, and comparing the change in amounts of the biomarkers, if any. For example, the biomarkers can be measured before and after drug administration or at two different time points during drug administration. The effect of therapy is determined based on these comparisons. If a treatment is effective, then the biomarkers will trend toward normal, while if treatment is ineffective, the biomarkers will trend toward disease indications. If a treatment is effective, then the biomarkers will trend toward normal, while if treatment is ineffective, the biomarkers will trend toward disease indications.

10. Use of Biomarkers for Peripheral Artery Disease in Screening Assays and Methods of Treating Peripheral Artery Disease The methods of the present invention have other applications as well. For example, the biomarkers can be used to screen for compounds that modulate the expression of the biomarkers in vitro or in vivo, which compounds in turn may be useful in treating or preventing peripheral artery disease in patients. In another example, the biomarkers can be used to monitor the response to treatments for peripheral artery disease. In yet another example, the biomarkers can be used in heredity studies to determine if the subject is at risk for developing peripheral artery disease.

Compounds suitable for therapeutic testing may be screened initially by identifying compounds which interact with beta-2-microglobulin and one or more biomarkers listed herein (e.g., lysozyme or cystatin C). By way of example, screening might include recombinantly expressing a biomarker, purifying the biomarker, and affixing the biomarker to a substrate. Test compounds would then be contacted with the substrate, typically in aqueous conditions, and interactions between the test compound and the biomarker are measured, for example, by measuring elution rates as a function of salt concentration. Certain proteins may recognize and cleave one or more biomarkers of Table 1, Table 2 or FIG. 3, in which case the proteins may be detected by monitoring the digestion of one or more biomarkers in a standard assay, e.g., by gel electrophoresis of the proteins.

In a related embodiment, the ability of a test compound to inhibit the activity of one or more of the biomarkers may be measured. One of skill in the art will recognize that the techniques used to measure the activity of a particular biomarker will vary depending on the function and properties of the biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibit or enhance the activity of a given biomarker may be determined by measuring the rates of catalysis in the presence or absence of the test compounds. The ability of a test compound to interfere with a non-enzymatic (e.g., structural) function or activity of beta-2-microglobulin, lysozyme, cystatin C or another one or more of the biomarkers herein may also be measured. For example, the self-assembly of a multiprotein complex which includes beta-2-microglobulin may be monitored by spectroscopy in the presence or absence of a test compound. Alternatively, if the biomarker is a non-enzymatic enhancer of transcription, test compounds which interfere with the ability of the biomarker to enhance transcription may be identified by measuring the levels of biomarker-dependent transcription in vivo or in vitro in the presence and absence of the test compound.

Test compounds capable of modulating the activity of any of the biomarkers of Table 1, Table 2 or FIG. 3 may be administered to patients who are suffering from or are at risk of developing peripheral artery disease. For example, the administration of a test compound which increases the activity of a particular biomarker may decrease the risk of peripheral artery disease in a patient if the activity of the particular biomarker in vivo prevents the accumulation of proteins for peripheral artery disease. Conversely, the administration of a test compound which decreases the activity of a particular biomarker may decrease the risk of peripheral artery disease in a patient if the increased activity of the biomarker is responsible, at least in part, for the onset of peripheral artery disease.

In an additional aspect, the invention provides a method for identifying compounds useful for the treatment of disorders such as peripheral artery disease which are associated with increased levels of modified forms of beta-2-microgbulin, lysozyme, or cystatin C. For example, in one embodiment, cell extracts or expression libraries may be screened for compounds which catalyze the cleavage of full-length beta-2-microglobulin to form truncated forms of beta-2-microglobulin. In one embodiment of such a screening assay, cleavage of beta-2-microglobulin may be detected by attaching a fluorophore to beta-2-microglobulin which remains quenched when beta-2-microglobulin is uncleaved but which fluoresces when the protein is cleaved. Alternatively, a version of full-length beta-2-microglobulin modified so as to render the amide bond between amino acids x and y uncleavable may be used to selectively bind or "trap" the cellular protease which cleaves full-length beta-2-microglobulin at that site in vivo. Methods for screening and identifying proteases and their targets are well-documented in the scientific literature, e.g., in Lopez-Ottin et al. (Nature Reviews, 3:509-519 (2002)).

In yet another embodiment, the invention provides a method for treating or reducing the progression or likelihood of a disease, e.g., peripheral artery disease, which is associated with the increased levels of truncated beta-2-microglobulin. For example, after one or more proteins have been identified which cleave full-length beta-2-microglobulin, combinatorial libraries may be screened for compounds which inhibit the cleavage activity of the identified proteins. Methods of screening chemical libraries for such compounds are well-known in art. See, e.g., Lopez-Otin et al. (2002). Alternatively, inhibitory compounds may be intelligently designed based on the structure of beta-2-microglobulin.

Full-length beta-2-microglobulin is believed to be involved in regulation of the body's iron stores, as well as in hereditary hemochromatosis, chronic renal insufficiency, and renal anemia. Beta-2-microglobulin expression is also induced as part of the body's immune response via the interleuking cascade. Because beta-2-microglobulin is highly processed from its pre-pro and pro-forms, it is likely that there are proteases which target and cleave it. Therefore, in a further embodiment, the invention provides methods for identifying compounds which increase the affinity of truncated beta-2-microglobulin for its target proteases. For example, compounds may be screened for their ability to cleave beta-2-microglobulin. Test compounds capable of modulating the cleavage of beta-2-microglobulin or the activity of molecules which interact with beta-2-microglobulin may then be tested in vivo for their ability to slow or stop the progression of peripheral artery disease in a subject.

At the clinical level, screening a test compound includes obtaining samples from test subjects before and after the subjects have been exposed to a test compound. The levels in the samples of one or more of the biomarkers listed in Table 1, Table 2 or FIG. 3 may be measured and analyzed to determine whether the levels of the biomarkers change after exposure to a test compound. The samples may be analyzed by mass spectrometry, as described herein, or the samples may be analyzed by any appropriate means known to one of skill in the art. For example, the levels of one or more of the biomarkers listed in Table 1, Table 2, or FIG. 3 may be measured directly by Western blot using radio- or fluorescently-labeled antibodies which specifically bind to the biomarkers. Alternatively, changes in the levels of mRNA encoding the one or more biomarkers may be measured and correlated with the administration of a given test compound to a subject. In a further embodiment, the changes in the level of expression of one or more of the biomarkers may be measured using in vitro methods and materials. For example, human tissue cultured cells which express, or are capable of expressing, one or more of the biomarkers of Table 1, Table 2 or FIG. 3 may be contacted with test compounds. Subjects who have been treated with test compounds will be routinely examined for any physiological effects which may result from the treatment. In particular, the test compounds will be evaluated for their ability to decrease disease likelihood in a subject. Alternatively, if the test compounds are administered to subjects who have previously been diagnosed with peripheral artery disease, test compounds will be screened for their ability to slow or stop the progression of the disease.

11. Examples 11.1. Example 1

Discovery of Biomarkers for PAD

The biomarkers of the present invention, including Beta 2-microglobulin, lysozyme, and cystatin C, were initially identified as a biomarker for PAD in a screening study using SELDI technology employing ProteinChip arrays from Ciphergen Biosystems, Inc. (Fremont, Calif.) ("Ciphergen"). The study set consisted of 45 patients with PAD and 43 patients without PAD. Subjects placed in the PAD group were those with an ankle-brachial index of 0.9 or less. Relevant traits in these groups are summarized and compared in FIG. 1. Patients in the PAD group were slightly older and generally had higher frequencies of cardiovascular risk factors.

Plasma samples were obtained from subjects in a fasting state. Each plasma sample was subjected to fractionation on a QhyperDF column before analysis using Ciphergen's ProteinChips, as described in the detailed protocol below. After fractionation, selected fractions were analyzed using Ciphergen's IMAC30 or CM10 ProteinChips. The spectra of polypeptides in the samples were generated by time-of-flight mass spectrometry on a Ciphergen PBSII mass spectrometer. Peak intensity values (1619 peaks/sample) were analyzed by Statistical Analysis of Microarrays (SAM) software.

The present study differs from studies which purport to show a relationship between $\beta_2$-microglobulin levels and symptoms such as arterial stiffness (see, e.g., Saijo et al., *Hypertens. Res.*, 28(6):505-511 (2005)). Those studies excluded from their trials subjects diagnosed with PDA and patients with low ABI (<0.9). Also, the studies relied on a pulse wave velocity (PWV) assay for including/excluding patients. The PWV assay measures vascular compliance and not arterial disease per se. While the arteries in the subjects used in Saijo et al.'s trials may have been less compliant than those of a "normal" subject, they were not necessarily the narrowed and/or clogged arteries of subjects with PAD.

Representative protocols used for fractionation, sample handling, and data acquisition are described below.

Q Hyper DF Anion Exchange Fractionation

Buffer List for anion exchange fractionation:

U1 (1M urea, 0.22% CHAPS, 50 mM Tris-HCl pH9)

50 mM Tris-HCl with 0.1% OGP pH9 (Wash buffer 1)

50 mM Hepes with 0.1% OGP pH7 (Wash buffer 2)

100 mM NaAcetate with 0.1% OGP pH5 (Wash buffer 3)

100 mM NaAcetate with 0.1% OGP pH4 (Wash buffer 4)

33.3% isopropanol/16.7% acetonitrile/0.1% trifluoracetic acid (Wash buffer 5)

Note: do not aliquot wash buffer 5 into the buffer tray until wash buffer 4 is being applied to the resin. This ensures that evaporation of the volatile organic solvents will not be an issue.

Material List:
Filter plate
5 v-well 96 well dishes, labeled F1-F5.
 a. Wash Resin
Prepare resin by washing Hyper Q DF resin (BioSepra, Cergy, France) 3 times with 5 bed volumes 50 mM Tris-HCl pH9. Then store in 50 mM Tris-HCl pH9 in a 50% suspension.
 b. Equilibrate Resin
Add 125 µL Hyper Q DF to each well in filter plate
Filter buffer
Add 150 µL U1 to each well
Filter buffer
Add 150 µL U1 to each well
Filter buffer
Add 150 µL U1 to each well
Filter buffer
 c. Bind Blood Plasma with Resin
Pipet 150 µL of sample from each tube to appropriate well in filter plate
Vortex 30' at 4°
 d. Collect Fractions
Place v-well 96 well plate F1 under filter plate
Collect flow-through in plate F1
Add 100 µL of wash buffer 1 to each well of filter plate
Vortex 10' at Room Temperature (RT)
Collect pH 9 eluant in plate F1
Fraction 1 contains the flow through and the pH 9 eluant.
Add 100 µL of wash buffer 2 to each well of filter plate
Vortex 10' at Room Temperature (RT)
Place v-well 96 well plate F2 under filter plate
Collect fraction 2 in plate F2
Add 100 µL of wash buffer 2 to each well of filter plate
Vortex 10' at Room Temperature (RT)
Collect remainder of fraction 2 in plate F2
Fraction 2 contains the pH 7 eluant.
Add 100 µL of wash buffer 3 to each well of filter plate
Vortex 10' at Room Temperature (RT)
Place v-well 96 well plate F3 under filter plate
Collect fraction 3 in plate F3
Add 100 µL of wash buffer 3 to each well of filter plate
Vortex 10' at Room Temperature (RT)
Collect remainder of fraction 3 in plate F3
Fraction 3 contains the pH 5 eluant.
Add 100 µL of wash buffer 4 to each well of filter plate
Vortex 10' at Room Temperature (RT)
Place v-well 96 well plate F4 under filter plate
Collect fraction 4 in plate F4
Add 100 µL of wash buffer 4 to each well of filter plate
Vortex 10' at Room Temperature (RT)
Collect remainder of fraction 4 in plate F4
Fraction 4 contains the pH 4 eluant.
Add 100 µL of wash buffer 5 to each well of filter plate
Vortex 10' at Room Temperature (RT)
Place v-well 96 well plate F5 under filter plate
Collect fraction 5 in plate F5
Add 100 µL of wash buffer 5 to each well of filter plate
Vortex 10' at Room Temperature (RT)
Collect remainder of fraction 5 in plate F5
Fraction 5 contains the organic solvent eluant.
Freeze until proceeding with chip binding protocol
 Chip Binding Protocol
Chip Washing Buffer List:
IMAC30 array (Ciphergen Biosystems, Inc.): a suitable wash includes, but is not limited to, 50 mM Tris pH 8.0 supplemented with 500 mM NaCl.
CM10 array (Ciphergen Biosystems, Inc.): a suitable wash includes, but is not limited to, 100 mM ammonium acetate pH 4.0
 Array Preparation:
Place arrays into bioprocessor
 Load IMAC30 arrays with copper
 Load 50 µl of $CuSO_4$ onto each spot of the IMAC30 array
 Vortex 15' at Room Temperature (RT)
 Remove $CuSO_4$ and repeat.
Water rinse
 Equilibrate Arrays:
Add 100 µl chip washing buffer appropriate to the array to each well
Vortex 5' at RT
Remove buffer after vortex
Add 100 µl chip washing buffer appropriate to the array to each well
Vortex 5' at RTk
Remove buffer after vortex
 Bind Plasma Fractions from Hyper Q DF Columns to Arrays:
Add 60 µl chip washing buffer appropriate to the array to each well
Add 20 µl plasma fraction
Vortex 30' at RT
Remove sample and buffer
 Wash Arrays:
Add 100 µl chip washing buffer appropriate to the array to each well
Vortex 5' at RT
Remove buffer after vortex
Add 100 µl chip washing buffer appropriate to the array to each well
Vortex 5' at RT
Remove buffer after vortex
Add 100 µl chip washing buffer appropriate to the array to each well
Vortex 5' at RT
Remove buffer after vortex
Water rinse 2 times
 Add Matrix:
Remove Bioprocessor top and gasket
Allow the arrays to dry
SPA:
Add 0.8 µl 50% SPA (sinapinic acid) in 50% Acetonitrile and 0.5% TFA
Air dry
Add 0.8 µl 50% SPA
Air dry
CHCA
Add 0.8 µl 20% CHCA dissolved in 50% Acetonitrile+0.5%
Air dry
Add 0.8 µl 20% CHCA
Air dry
 Data Acquisition Settings
Energy absorbing molecule: 50% SPA
Set high mass to 100000 Daltons, optimized from 2000 Daltons to 100000 Daltons.
Set starting laser intensity to 200.
Set starting detector sensitivity to 8.
Focus mass at 8000 Daltons.
Set Mass Deflector to 1000 Daltons.
Set data acquisition method to Seldi Quantitation
Set Seldi acquisition parameters 20. delta to 4. transients per to 10 ending position to 80.
Set warming positions with 2 shots at intensity 225 (don't include warming shots).

Process sample.

Measurement and Analysis of Biomarker Peak Intensities

Significance Analysis for Microarrays software ("SAM") was used to identify a set of significant peaks. SAM is described in detail in Tusher et al. (*PNAS* (2001) 98: 5116-5121). The results of the SAM analysis are presented in FIG. 2. FIG. 2 shows that 11 out of 1619 biomarkers were identified as differing significantly between the PAD and non-PAD groups.

Figure 6:
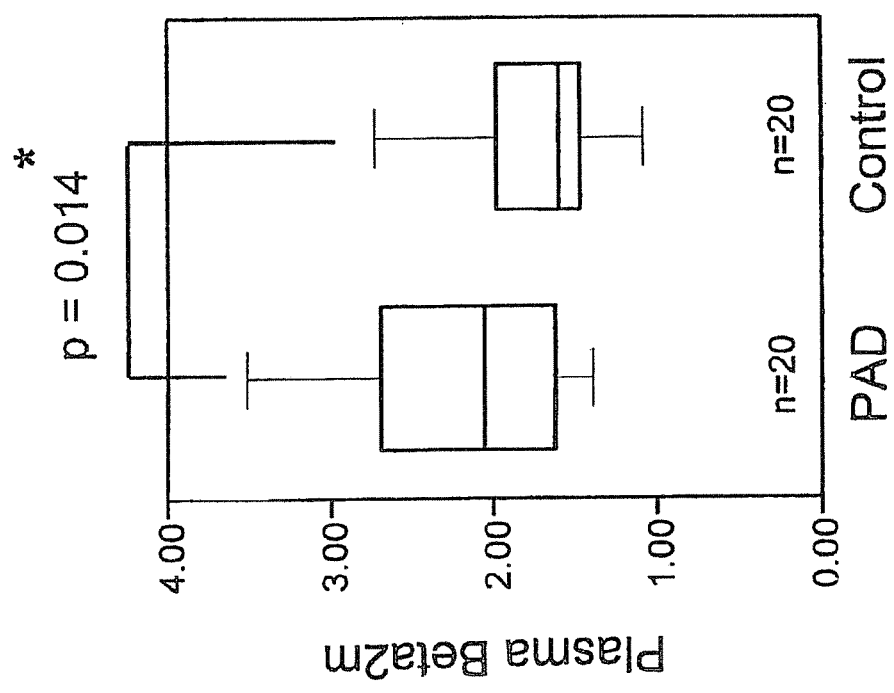
FIG. 6 shows results of a Mann-Whitney nonparametric statistical analysis of plasma and serum beta 2-microglobulin levels in PAD and control subjects, as measured using an ELISA assay.

FIG. 3 shows a table that summarizes data relating to the 11 proteins identified in the SAM analysis discussed above, including the chip and QHyper DF fraction in which the protein was found. As indicated in the boxed area of the table of FIG. 3, 6 of the 11 proteins matched the mass spectrometry fingerprint of beta 2-microglobulin. Experimental molecular weights are calculated based on the mass spectrometric data, while the Calculated molecular weights in the table are determined from the known amino acid composition of beta 2-microglobulin and, where indicated, the mass, of an SPA adduct. Table 2, also summarizes the data relating to the 11 significant proteins in FIG. 2, and includes the exact p values of linear regression analysis between ABI values and peak intensities for the selected differentially expressed proteins.

available ELISA kit. FIG. 6 shows that plasma and serum beta 2-microglobulin levels were significantly higher in PAD patients than control subjects, using a Maim-Whitney non-parametric test.

Figure 7:
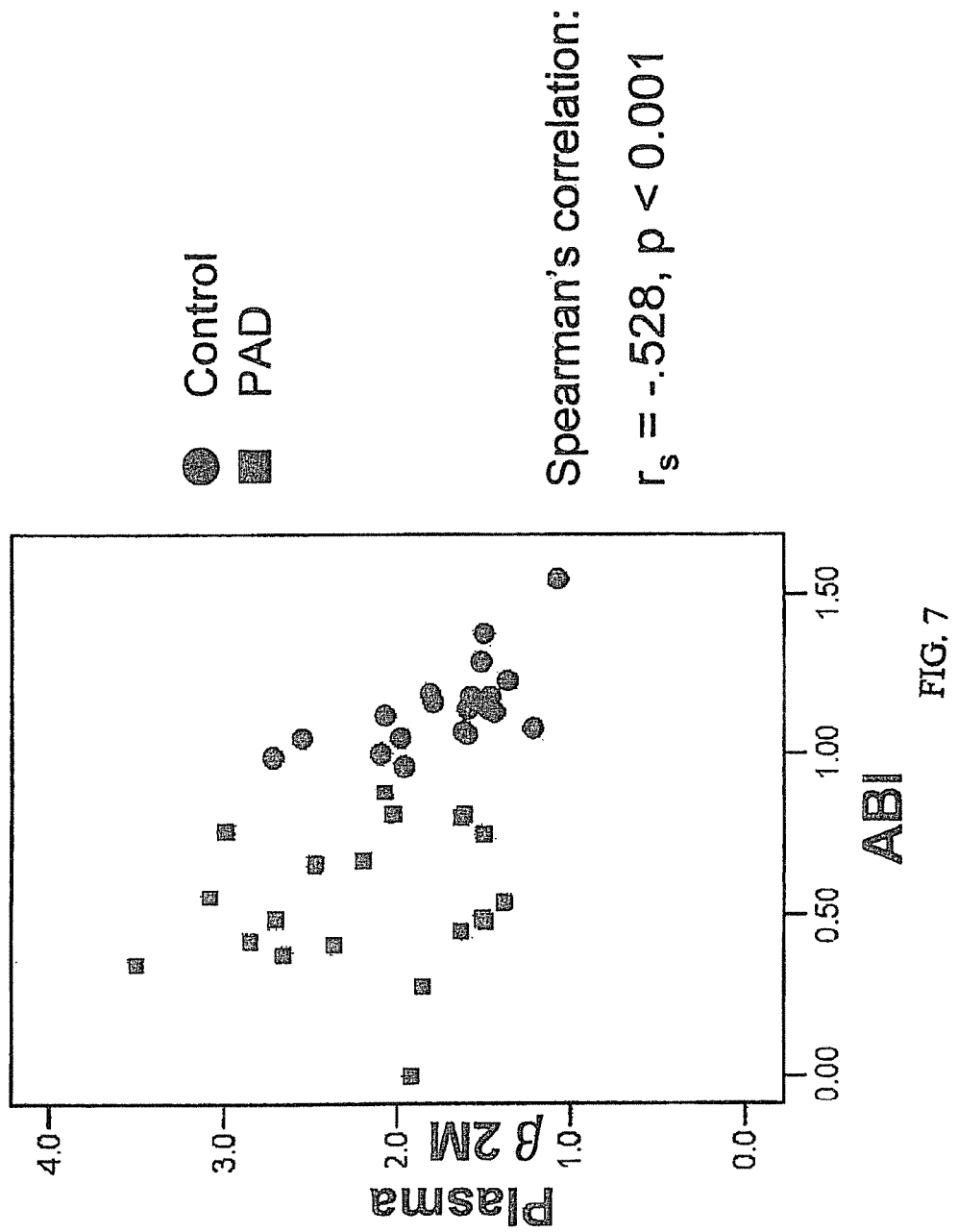
FIG. 7 shows the results of a Spearman's Rank Correlation analysis of the relationship between patients' ABI measurements and beta 2-microglobulin levels as measured by ELISA.
Figure 10:
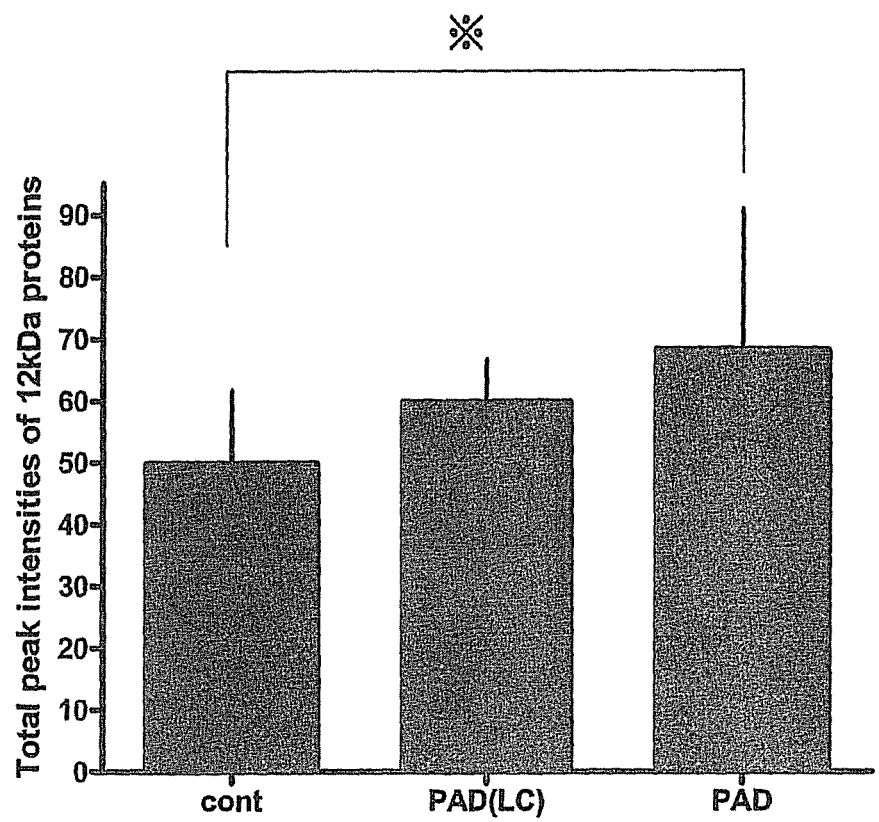
FIG. 10 shows ACT (average claudication time) compared to total peak intensities of the six beta-2-microglobulin proteins in subjects with or without PAD. Control, n=43, i.e., no claudication during exercise; PAD (LC)>12 minutes, n=6; PAD<12 minutes, n=39. Total peak intensities are represented in arbitrary units. The mean difference is significant at the p<0.05 level by Bonferroni multiple comparison. (*) represent differences between groups by one-way ANOVA with Bonferroni correction, with p values P<0.05. Error bars show standard deviations.

FIG. 7 shows the results of a Spearman's Rank Correlation analysis. The results show that there is a strong negative correlation (r<−0.5) between beta 2-microglobulin levels and ABI. A relationship was also observed between peak intensity of β2 m and claudication time, as shown in FIG. 10 (ACT; groups being normal subjects without claudication; PAD with absolute ACT >12 minutes; or PAD with ACT <12 minutes).

A linear regression analysis of the data showed that, among traditional risk factors for cardiovascular disease, a history of smoking, hyperlipidemia, and diabetes were statistically significant univariate predictors of ankle-brachial index. In addition, glomerular filtration rate had a positive trend toward a correlation with ankle-brachial index. Beta 2-microglobulin, transformed logarithmically to reduce skewness, was strongly correlated with ankle-brachial index. The results are summarized in FIG. 8.

Using the listed variables in FIG. 8 with significance values less than 0.2, a multivariate model was created to assess the independent relationship between log beta 2-microglobulin

TABLE 2

Exact P values of linear regresson between the peak intesitis and the ABI for selected differentially expressed proteins in discovery data sets

| m/Z | Conditions | Putative protein | Mean Peak Intensities | | | Correlation with ABI | |
|---|---|---|---|---|---|---|---|
| | | | PAD | Control | P value | rs | P |
| 11,732 | CM10-pH 7 | Beta-2-microglobulin | 2.842 ± 0.167 | 2.028 ± 0.116 | <0.001 | −0.491 | <0.001 |
| 11,731 | CM10-pH 7 | Beta-2-microglobulin | 9.902 ± 0.489 | 7.769 ± 0.454 | 0.002 | −0.419 | <0.001 |
| 11,722 | IMAC30-pH 7 | Beta-2-microglobulin | 11.367 ± 0.716 | 8.644 ± 0.588 | 0.004 | −0.366 | 0.001 |
| 11,731 | IMAC30-pH 5 | Beta-2-microglobulin | 13.883 ± 1.613 | 7.543 ± 0.484 | <0.001 | −0.401 | <0.001 |
| 11,811 | IMAC30-pH 9 | Beta-2-microglobulin, | 24.915 ± 0.683 | 21.214 ± 0.928 | 0.005 | −0.287 | 0.007 |
| 11,941 | IMAC30-pH 5 | Beta-2-microglobulin, | 3.943 ± 0.353 | 2.543 ± 0.136 | <0.001 | −0.410 | <0.001 |
| 13,339 | CM10-pH 9 | Cystatin C | 4.802 ± 0.291 | 3.662 ± 0.144 | 0.001 | −0.330 | 0.002 |
| 14,690 | CM10-pH 9 | Lysozyme C | 2.975 ± 0.201 | 2.152 ± 0.147 | 0.02 | −0.374 | <0.001 |
| 22,519 | CM10-pH 7 | most likely IgG light chain | 2.809 ± 0.119 | 2.211 ± 0.138 | <0.001 | −0.504 | <0.001 |
| 22,999 | CM10 | Not determined | 6.576 ± 0.311 | 5.3852 ± 0.247 | 0.004 | −0.351 | 0.001 |
| 36,067 | CM10-pH 4 | Not determined | 0.477 ± 0.036 | 0.353 ± 0.016 | 0.003 | −0.225 | 0.037 |

Figure 4:
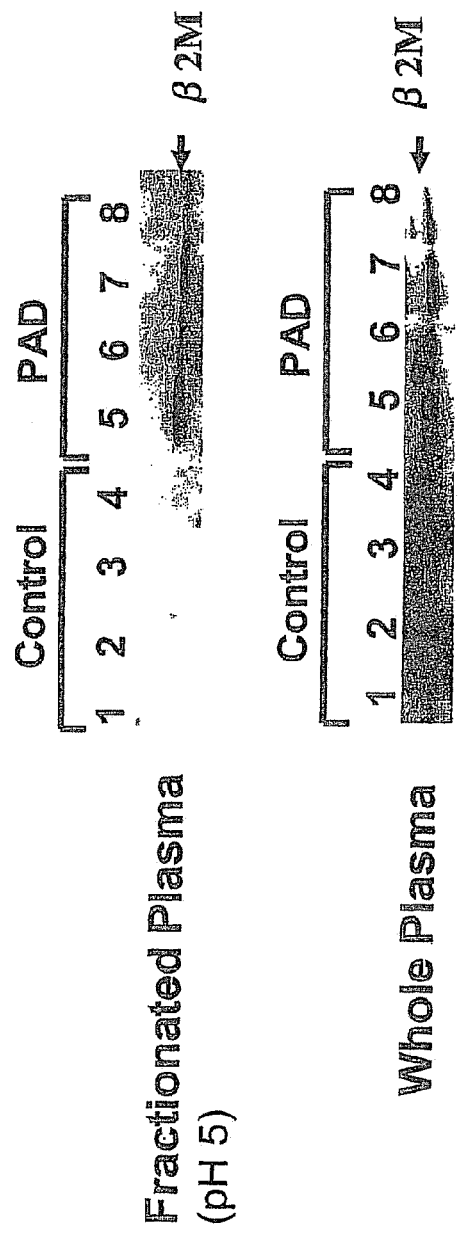
FIG. 4 shows results of a Western blot of beta 2-microglobulin concentrations in samples from 4 patients with PAD compared to samples from 4 control subjects.

11.2. Western Blot Analysis of Beta 2-Microglobulin Overexpression In PAD Patients Using western blot and an anti-beta2 microglobulin antibody, higher beta 2-microglobulin concentrations were observed in samples from 4 patients with PAD compared to samples from 4 control subjects. The results are shown in FIG. 4. This finding is consistent when using plasma fractionated at pH 5 or using whole, unfractionated plasma.

11.3. Confirmation Study

A confirmation study was conducted to confirm that the observed correlation was not confounded by other patient traits (e.g., other cardiovascular risk factors, renal function, etc.). For this confirmation study, plasma was obtained from 20 patients with PAD and 20 control subjects who had no clinical evidence of PAD or coronary disease. FIG. 5 shows a table which summarizes the patients in the two groups. The patients in the two comparison groups were similar in age and gender. However, as expected, the PAD group had higher frequencies of cardiovascular risk factors and a trend toward lower glomerular filtration rate.

All plasma was obtained from patients in the fasting state. Beta 2-microglobulin was measured using a commercially and ankle-brachial index. This analysis confirms an independent relationship between high beta 2-microglobulin levels and a lower ankle-brachial index, as shown in FIG. 9. Specifically, the results show that log beta 2-microglobulin levels remain independently associated in an inverse manner with the ankle-brachial index, even after adjustment for the potential confounding effects of lower glomerular filtration rates in PAD patients. This model predicted an estimated 45% of the variance of ankle-brachial index observed this study.

11.4. Validation Study in a Population at Risk for PAD

In patients undergoing coronary angiography, without known PAD status (n=237), serum β2 m was higher in patients with PAD. ABI was determined prior to a comprehensive clinical characterization which included questionnaires to elicit demographics, ethnicity, quality of life, functional capacity; venipuncture for plasma, serum and genomic DNA; and coronary angiography. Patients with PAD had an ABI at rest of <0.90, or in those with non-compressible ankle arteries, a toe-brachial index of <0.60. Glomerular filtration rate (GFR) was estimated by the Modification of Diet in Renal Disease Study (MDRD) method 14. Beta-2-microglobulin levels correlated with ABI independent of other vascular risk factors and GFR by multivariate regression analysis (Table 3).

TABLE 3

Multivariate Regression for Predictors of Index ABI (n = 273)
Dependent Variable: Index Ankle Brachial Index
Significant Independent Correlations Bolded

|  | Coefficient | Standard Error | p value |
|---|---|---|---|
| Constant | 1.4030 | 0.1569 | <0.001 |
| Age | −0.0012056 | 0.0002556 | 0.010 |
| Diabetes | −0.05948 | 0.02738 | <0.001 |
| History of Smoking | −0.05948 | 0.02738 | 0.031 |
| Hypertension | 0.0000321 | 0.0003223 | 0.921 |
| Hyperlipidemia | −0.0000577 | 0.0002753 | 0.834 |
| Gender | 0.0000352 | 0.0002369 | 0.882 |
| Body Mass Index | 0.002556 | 0.002749 | 0.354 |
| GFR | −0.0003144 | 0.0005261 | 0.551 |
| Log β2M | −0.019535 | 0.008783 | 0.027 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for qualifying peripheral artery disease status in a subject comprising:
   (a) measuring lysozyme in a biological sample from the subject; and
   (b) correlating the measurement or measurements with peripheral artery disease versus non-peripheral artery disease.

2. The method of claim 1, further comprising measuring β2-microglobulin.

3. The method of claim 1, wherein said measurement or measurements of a biomarker is performed using mass spectrometry or an immunoassay.

4. The method of claim 1, further comprising measuring cystatin C or β2-microglobulin.

5. The method of claim 3, wherein mass spectrometry is SELDI-MS.

6. The method of claim 1, wherein the sample is blood, serum, or plasma.

7. The method of claim 1, wherein the correlating is performed by executing a software classification algorithm.

8. The method of claim 1, further comprising: (c) reporting the status to the subject.

9. The method of claim 1, further comprising: (c) recording the status on a tangible medium.

10. The method of claim 1, further comprising: (c) managing subject treatment based on the status.

11. The method of claim 1, further comprising: (d) measuring the at least one biomarker after subject management and correlating the measurement with disease progression.

\* \* \* \* \*